United States Patent
Craig

(10) Patent No.: US 9,028,484 B2
(45) Date of Patent: May 12, 2015

(54) FINGERTIP ELECTROSURGICAL INSTRUMENTS FOR USE IN HAND-ASSISTED SURGERY AND SYSTEMS INCLUDING SAME

(75) Inventor: Jason L. Craig, Loveland, CO (US)

(73) Assignee: Covidien LP, Mansfield, MA (US)

( * ) Notice: Subject to any disclaimer, the term of this patent is extended or adjusted under 35 U.S.C. 154(b) by 1213 days.

(21) Appl. No.: 12/947,420

(22) Filed: Nov. 16, 2010

(65) Prior Publication Data

US 2012/0123410 A1  May 17, 2012

(51) Int. Cl.
| | | |
|---|---|---|
| A61B 18/14 | (2006.01) | |
| A61B 18/18 | (2006.01) | |
| A61B 19/04 | (2006.01) | |
| A61B 17/00 | (2006.01) | |
| A61B 18/00 | (2006.01) | |
| A61B 19/00 | (2006.01) | |

(52) U.S. Cl.
CPC ............. *A61B 18/14* (2013.01); *A61B 18/18* (2013.01); *A61B 19/04* (2013.01); *A61B 2017/00115* (2013.01); *A61B 2018/00577* (2013.01); *A61B 2018/00589* (2013.01); *A61B 2018/00595* (2013.01); *A61B 2018/00601* (2013.01); *A61B 2018/0063* (2013.01); *A61B 2018/00791* (2013.01); *A61B 2019/261* (2013.01); *A61B 2017/00438* (2013.01)

(58) Field of Classification Search
CPC ............ A61B 2019/261; A61B 2019/00438; A61B 18/1402
USPC ........................................ 606/32–52
See application file for complete search history.

(56) References Cited

U.S. PATENT DOCUMENTS

| 206,474 | A | * | 7/1878 | Morel .............................. 601/15 |
|---|---|---|---|---|
| 3,845,771 | A | * | 11/1974 | Vise ................................ 606/49 |
| D263,020 | S | | 2/1982 | Rau, III |
| 4,337,496 | A | * | 6/1982 | Laird ............................. 361/232 |
| 4,510,939 | A | * | 4/1985 | Brenman et al. .............. 600/384 |
| D295,893 | S | | 5/1988 | Sharkany et al. |
| D295,894 | S | | 5/1988 | Sharkany et al. |
| 4,765,343 | A | * | 8/1988 | Brenman et al. .............. 600/384 |
| 5,242,440 | A | * | 9/1993 | Shippert ......................... 606/30 |

(Continued)

FOREIGN PATENT DOCUMENTS

| CN | 1103807 | 6/1995 |
|---|---|---|
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Joseph Stoklosa
*Assistant Examiner* — Jocelyn D Ram

(57) ABSTRACT

A fingertip-mountable electrosurgical instrument includes a monopolar electrode capable of directing energy into tissue, and a holder configured to be operably coupled to the monopolar electrode. The holder is also configured to be operably coupled to an energy source. The holder includes a housing body and one or more attachment members coupled to the housing body. The one or more attachment members are configured to be removeably attachable to a user's finger. The housing body includes a distal end and a proximal end. The monopolar electrode is mechanically coupled to the distal end of the housing body.

19 Claims, 10 Drawing Sheets

(56) References Cited

U.S. PATENT DOCUMENTS

| | | | |
|---|---|---|---|
| 5,693,041 A * | 12/1997 | Murphy-Chutorian | 606/2 |
| 5,986,446 A * | 11/1999 | Williamson | 324/157 |
| D424,694 S | 5/2000 | Tetzlaff et al. | |
| D425,201 S | 5/2000 | Tetzlaff et al. | |
| 6,183,467 B1 | 2/2001 | Shapeton et al. | |
| D449,886 S | 10/2001 | Tetzlaff et al. | |
| D457,958 S | 5/2002 | Dycus et al. | |
| D457,959 S | 5/2002 | Tetzlaff et al. | |
| D496,997 S | 10/2004 | Dycus et al. | |
| D499,181 S | 11/2004 | Dycus et al. | |
| 6,902,536 B2 | 6/2005 | Manna et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| D564,662 S | 3/2008 | Moses et al. | |
| D606,203 S | 12/2009 | Husheer et al. | |
| D613,412 S | 4/2010 | DeCarlo | |
| 2004/0153121 A1 | 8/2004 | Pietrabissa et al. | |
| 2004/0193211 A1* | 9/2004 | Voegele et al. | 606/205 |
| 2004/0225217 A1 | 11/2004 | Voegele et al. | |
| 2004/0260281 A1* | 12/2004 | Baxter et al. | 606/41 |
| 2005/0020884 A1 | 1/2005 | Hart et al. | |
| 2007/0060919 A1 | 3/2007 | Isaacson et al. | |
| 2007/0093807 A1* | 4/2007 | Baxter et al. | 606/41 |
| 2008/0167680 A1* | 7/2008 | Voegele et al. | 606/206 |
| 2008/0243174 A1* | 10/2008 | Oren et al. | 606/205 |
| 2010/0204640 A1* | 8/2010 | Mingozzi et al. | 604/21 |
| 2012/0123404 A1* | 5/2012 | Craig | 606/33 |
| 2012/0123405 A1* | 5/2012 | Moua et al. | 606/33 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO 2010/035831 | 4/2010 |

OTHER PUBLICATIONS

U.S. Appl. No. 08/483,742, filed Jun. 7, 1995, Roger A. Stern.
U.S. Appl. No. 12/582,857, filed Oct. 21, 2009, Charles D. Allen.
U.S. Appl. No. 12/606,769, filed Oct. 27, 2009, Joseph D. Brannan.
U.S. Appl. No. 12/607,221, filed Oct. 28, 2009, Joseph D. Brannan.
U.S. Appl. No. 12/607,268, filed Oct. 28, 2009, Joseph D. Brannan.
U.S. Appl. No. 12/619,323, filed Nov. 16, 2009, Arnold V. DeCarlo.
U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.
U.S. Appl. No. 12/708,974, filed Feb. 19, 2010, Joseph D. Brannan.
U.S. Appl. No. 12/709,014, filed Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 12/732,521, filed Mar. 26, 2010, Steven Kim.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.

(56) References Cited

OTHER PUBLICATIONS

U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/877,182, filed Sep. 8, 2010, Robert B. Cunningham.
U.S. Appl. No. 12/910,442, filed Oct. 22, 2010, Robert B. Cunningham.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With The LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., Theoretical Aspects of "Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•LInear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.

(56) References Cited

OTHER PUBLICATIONS

Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98955575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.

(56) References Cited

OTHER PUBLICATIONS

European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.

\* cited by examiner

FINGERTIP ELECTROSURGICAL INSTRUMENTS FOR USE IN HAND-ASSISTED SURGERY AND SYSTEMS INCLUDING SAME

BACKGROUND

1. Technical Field

The present disclosure relates to electrosurgical instruments and, more particularly, to fingertip electrosurgical instruments for use in hand-assisted surgery, such as hand-assisted laparoscopic surgery (HALS), and systems including the same.

2. Discussion of Related Art

Electrosurgical instruments have become widely used by surgeons. Electrosurgery involves application of high-frequency electrical current to a surgical site to cut, ablate, coagulate, cauterize or seal tissue.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue, and a patient return electrode (usually a plate positioned on the patient's thigh or back) as the means to complete the electrical circuit between the electrosurgical generator and the patient. In bipolar electrosurgery, the electrosurgical device includes two electrodes that are located in proximity to one another for the application of current between their surfaces. Bipolar electrosurgical current travels from one electrode, through the intervening tissue to the other electrode to complete the electrical circuit.

Bipolar instruments may include end effectors, such as grippers, cutters, forceps, dissectors and the like, which often have a limited range of motion, e.g., due to mechanical design constraints. This limited range of motion may be undesirable to a surgeon working in an area that requires a complex series of movements. In such situations, it may be desirable to use bipolar instruments that facilitate a wide and variable range of motion to allow for complex surgical articulation. The mechanical nature of bipolar instruments may limit the amount of tactile sensory feedback received by the surgeon during a procedure. In certain procedures, it may be useful to have the ability to determine how much pressure to apply to a cutting or coagulation surface.

Surgical techniques and instruments have been developed that allow the surgeon to perform an increasing range of surgical procedures with minimal incisions into the skin and body tissue of the patient. Minimally-invasive surgery has become widely accepted in many medical specialties, often replacing traditional open surgery. Unlike open surgery, in which a long incision is made to expose the area of the body to be operated on, minimally-invasive procedures, such as endoscopy or laparoscopy, are performed through one or more short incisions, with much less trauma to the body. The number of incisions may depend on the type of surgery. It is not uncommon for some abdominal operations, e.g., gallbladder surgery, to be performed through a single incision. Although minimally-invasive techniques vary widely, surgeons generally rely on a lighted camera at the tip of a tube or cannula to send a two-dimensional image of the surgical site to a high-definition monitor, which the surgeon watches throughout the operation. In most patients, the minimally-invasive approach leads to decreased postoperative pain, shorter hospital stay, faster recovery, decreased incidence of wound-related and pulmonary complications, cost savings by reducing post-operative care, and, in some cases, a better overall outcome.

Minimally-invasive surgical procedures are performed throughout the body and generally rely on obtaining access to an internal surgical site through a relatively small pathway, often less than one centimeter in diameter, to the surgical site. One method of providing such a pathway is by inserting a trocar assembly through the skin of the patient. Commonly, to place the trocar cannula, the penetrating tip of the obturator of the trocar is pushed through the skin and underlying tissue until the distal end of the cannula is within the body cavity. Alternatively, some trocar devices have a blunt obturator for placing the cannula through a previously-made incision. Once the trocar has been properly positioned, the obturator is removed and the cannula is then available as a pathway between the surgical site and the exterior of the patient's body through which the surgeon may introduce the various surgical instruments required to perform the desired procedures. Surgical instruments insertable through cannulae include forceps, clamps, scissors, probes, flexible or rigid scopes, staplers and cutting instruments.

In some procedures, a wall of a body cavity is raised by pressurization of the body cavity to provide sufficient working space at the surgical worksite and/or to allow a trocar to penetrate the body cavity without penetrating an organ within the cavity. The process of distending the abdomen wall from the organs enclosed in the abdominal cavity is referred to as insufflation. During a laparoscopic procedure (endoscopy in the abdominal cavity), insufflation is achieved by introducing an insufflation gas, such as carbon dioxide, nitrogen, nitrous oxide, helium, argon, or the like, through a Veress needle or other conduit inserted through the abdominal wall.

Minimally-invasive surgery has become the standard-of-care for certain surgical procedures, but it has not been widely adopted for more complex or delicate procedures for several reasons. Advanced laparoscopic procedures often take much longer than conventional surgery. This partly reflects the limited instrumentation available for advanced laparoscopic surgery, as well as the lack of tactile sensory feedback and the absence of depth perception, which is inherent in viewing a two-dimensional image on a monitor. The loss of the ability to place the hand into the abdomen during laparoscopic surgery may limit the use of laparoscopy for complex abdominal surgery.

Some surgical procedures, e.g., simple to complex intra-abdominal operations, may be appreciably facilitated by the introduction of a hand into the laparoscopic arena. The human hand is capable of performing many functions during surgery that are difficult to reproduce with laparoscopic instruments.

In hand-assisted laparoscopic surgery (HALS), the surgeon inserts a hand through a small incision via a pressurized sleeve into the insufflated region and uses the hand for sensory perception and to assist the laparoscopic instruments directly, while observing the entire procedure on a monitor. Most surgeons insert the non-dominant hand, but the dominant hand may be used. A hand-assisted technique may be useful in a variety of procedures, including minimally-invasive colorectal surgery, splenectomy for splenomegaly, living donor nephrectomy, and procedures considered too complex for a laparoscopic approach. HALS may offer the ability to perform more complex operations more safely by allowing tactile sensory feedback and depth perception, gentle traction and counter-traction on tissues, digital blunt dissection, hemorrhage control and identification of vessels, structures and tissue planes.

Fingertip electrosurgical instruments for use in hand-assisted surgery such as HALS may be useful in a variety of procedures and operations, and may enhance the suitability of laparoscopy for complex abdominal surgery.

SUMMARY

The present disclosure relates to a fingertip-mountable electrosurgical instrument including a monopolar electrode capable of directing energy into tissue, and a holder configured to be operably coupled to the monopolar electrode. The holder is further configured to be operably coupled to an energy source. The holder includes a housing body and one or more attachment members coupled to the housing body. The one or more attachment members are configured to be removeably attachable to a user's finger. The housing body includes a distal end and a proximal end. The monopolar electrode is mechanically coupled to the distal end of the housing body.

The present disclosure also relates to an electrosurgical instrument including a surgical glove, a monopolar electrode capable of directing energy into tissue, and a holder configured to be operably coupled to the monopolar electrode. The holder is also configured to be operably coupled to an energy source. The holder includes a housing body and an attachment member coupled to the housing body. The attachment member is configured to couple the holder to the surgical glove. The monopolar electrode is mechanically coupled to the housing body.

The present disclosure also relates to an electrosurgical system including an energy source and a fingertip-mountable electrosurgical instrument operably coupled to the energy source. The fingertip-mountable electrosurgical instrument includes a monopolar electrode capable of directing energy into tissue and a holder configured to be operably coupleable with the monopolar electrode. The holder is also configured to support the monopolar electrode such that the monopolar electrode extends longitudinally from a distal end of a user's fingertip.

BRIEF DESCRIPTION OF THE DRAWINGS

Objects and features of the presently disclosed fingertip electrosurgical instruments for use in hand-assisted surgery and systems including the same will become apparent to those of ordinary skill in the art when descriptions of various embodiments thereof are read with reference to the accompanying drawings, of which.

DETAILED DESCRIPTION

Figure 1:
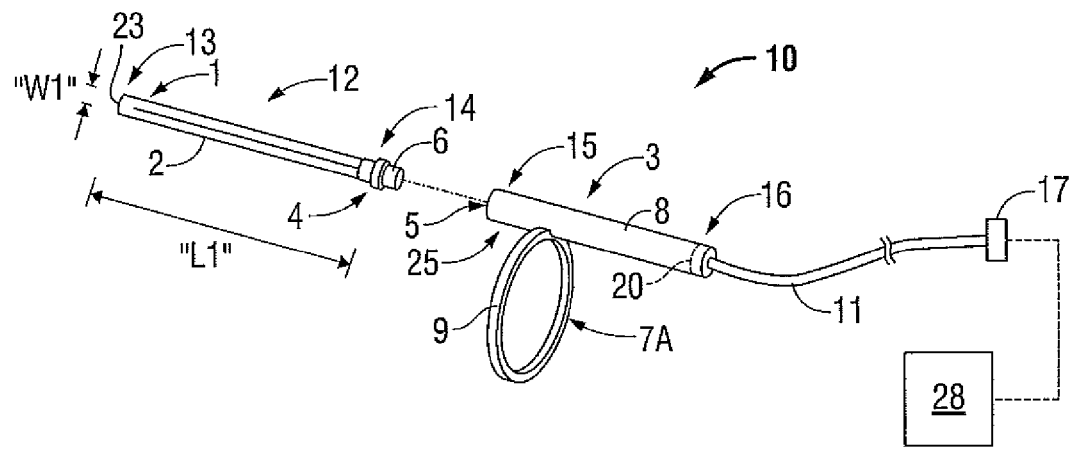
FIG. 1 is a perspective view of a fingertip, monopolar electrosurgical instrument, with parts separated, according to an embodiment of the present disclosure.

Hereinafter, embodiments of fingertip electrosurgical instruments for use in hand-assisted surgery and systems including the same of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3\times10^8$ cycles/second) to 300 gigahertz (GHz) ($3\times10^{11}$ cycles/second). As it is used in this description, "ablation procedure" generally refers to any ablation procedure, such as, for example, microwave ablation, radiofrequency (RF) ablation, or microwave or RF ablation-assisted resection. As it is used in this description, "energy applicator" generally refers to any device that can be used to transfer energy from a power generating source, such as a microwave or RF electrosurgical generator, to tissue. As it is used in this description, "transmission line" generally refers to any transmission medium that can be used for the propagation of signals from one point to another. As it is used in this description, "fluid" generally refers to a liquid, a gas or both.

As it is used in this description, "finger" generally refers to the terminating members of the hand including the thumb. In general, the term "finger" is interchangeable, in this disclosure, with the terms "surgeon's finger" and "user's finger". As it is used in this description, "tip segment" generally refers to that portion of a finger including the distal phalange (also known as the third phalange). As it is used in this description, "middle segment" generally refers to that portion of a finger including the second phalange. As it is used in this description, "base segment" generally refers to that portion of a finger including the proximal phalange (also known as the first phalange). As it is used in this description, "top knuckle" generally refers to the distal interphalangeal joint. As it is used in this description, "middle knuckle" generally refers to the proximal interphalangeal joint. For the purposes herein, the term "first knuckle" is interchangeable with the term "top knuckle", and the term "second knuckle" is interchangeable with the term "middle knuckle". As it is used in this description, "fingertip" generally refers to the tip segment, or portion thereof, but may also include the first knuckle and the middle segment, or portion thereof.

Various embodiments of the present disclosure provide fingertip, monopolar electrosurgical instruments for directing energy into tissue. Various embodiments of the present disclosure provide fingertip, bipolar electrosurgical instruments for directing energy into tissue. Embodiments may be suitable for utilization with hand-assisted, endoscopic and laparoscopic surgical procedures. Embodiments may be suitable for utilization in open surgical applications Embodiments may be implemented using electromagnetic radiation at microwave frequencies, RF frequencies or at other frequencies. Fingertip, monopolar and bipolar electrosurgical instruments, according to various embodiments, are designed and configured to operate between about 300 MHz and about 10 GHz.

Various embodiments of the presently disclosed fingertip, monopolar electrosurgical instrument including an energy applicator are suitable for microwave or RF ablation and for use to pre-coagulate tissue for microwave or RF ablation-assisted surgical resection.

Figure 3:
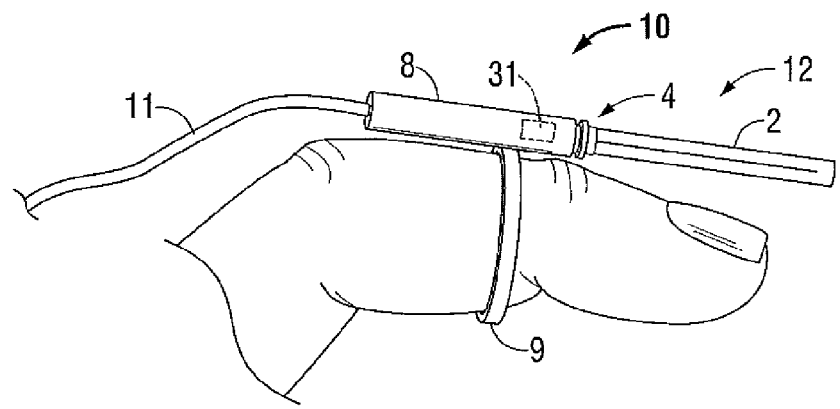
FIG. 3 is a perspective view of the fingertip, monopolar electrosurgical instrument of FIG. 1 shown coupled to a surgeon's finger according to an embodiment of the present disclosure.

A fingertip, monopolar electrosurgical instrument 10 according to an embodiment of the present disclosure is shown in FIG. 1 and includes an electromagnetic energy delivery device or energy applicator 12. FIG. 3 shows the fingertip, monopolar electrosurgical instrument 10 coupled to the middle segment of a surgeon's finger.

Energy applicator 12 includes an elongated, electrically-conductive element 2 (also referred to herein as a "monopolar electrode", or, simply, "electrode") connected by a holder 3 via a transmission line 11 to a connector 17, which may further operably connect the energy applicator 12 to an electrosurgical power generating source 28. Holder 3 generally includes a housing body 8 and an attachment member 7A configured to allow coupling of the holder 3 to a surgeon's finger.

In embodiments, the housing body 8 is adapted to provide an electrical connection between the electrode 2 and the transmission line 11. In embodiments, the housing body 8 has a substantially cylindrical shape, and may be formed as a substantially hollow tubular body. Portions of the housing body 8 may include an electrically non-conductive material. Housing body 8 includes a distal end 15 and a proximal end 16.

In some embodiments, the monopolar electrode 2 is configured to be removeably coupleable with the holder 3, which allows for selective replacement of the electrode 2 (or the housing body 8 and the attachment member 7A). In other embodiments, the electrode 2 is permanently affixed to the holder 3, e.g., by a locking screw, a permanent adhesive, or other devices or processes to make a secure or permanent attachment.

Fingertip, monopolar electrosurgical instrument 10 may include a switch (not shown) configured to permit the user to selectively activate the energy applicator 12. An actuator may additionally, or alternatively, be provided that is adapted to facilitate operative coupling with the electrosurgical power generating source 28. The actuator may be any suitable actuator, such as, without limitation, a footswitch, a handswitch, an orally-activated switch (e.g., a bite-activated switch and/or a breath-actuated switch), and the like.

Fingertip, monopolar electrosurgical instrument 10 may be designed such that it is fully or partially disposable depending upon a particular purpose or to achieve a particular result. For example, the monopolar electrode 2 may be selectively and releasably engageable with the distal end 15 of the housing body 8. In such case, the fingertip, monopolar electrosurgical instrument 10 would be considered "partially disposable" or "reposable", e.g., a new or different monopolar electrode 2 selectively replaces the old monopolar electrode 2 as needed.

Monopolar electrode 2 may be formed of any suitable electrically-conductive material (e.g., metal such as stainless steel, aluminum, platinum, titanium, copper, gold or silver) of any suitable length. Monopolar electrode 2 may have a suitable length "L1" in a range from about 0.1 inches to about 3.0 inches. Electrode 2 may have a suitable width "W1" in a range from about 0.05 inches to about 0.50 inches. Electrode 2 includes a distal end 13 and a proximal end 14, and may have a substantially cylindrical shape. The shape, size and number of electrode 2 may be varied from the configuration depicted in FIG. 1.

Located at the distal end 13 of the monopolar electrode 2 is an end portion 1, which may terminate in a flat tip 23. The end portion 1 may include other shapes, such as, for example, a tip 23 that is bulbous, rounded, square, hexagonal, or cylindro-conical. Electrode 2 may take any number of shapes for a number of reasons, e.g., depending upon the type of surgical procedure and/or surgeon's preference.

Located at the proximal end 14 of the electrode 2 is a connector 4. Connector 4 is adapted to mechanically and electrically couple the electrode 2 to the holder 3. Connector 4 includes a connector rod 6 having a cylindrical, square or any other suitable configuration. Connector rod 6 may be releaseably engageable with an opening or socket 5 defined in the holder 3. The connector rod 6 may have any suitable dimensions, and may include a threaded portion (not shown). It will be appreciated that, in an alternative embodiment, the holder 3 may be configured with a connector rod adapted to matingly engage with an opening or socket defined in the electrode 2.

In embodiments, the housing body 8 includes an electrode-engagement portion 25 defining an interior opening 5. The electrode-engagement portion 25, or portion thereof, may be threaded for mating engagement with a threaded connector rod 6. Electrode 2 may be electrically coupled to the electrode-engagement portion 25 by friction fit, solder or other suitable electrical connection.

Holder 3 includes an electrical current input terminal 20 disposed within the housing body 8. Current input terminal 20 is configured to be operably coupled to the transmission line 11. Current input terminal 20 may be disposed at any suitable position within the housing body. In an embodiment, the current input terminal 20 is disposed at the proximal end 16 of the holder 3. In embodiments, the housing body 8 is configured to operably couple the monopolar electrode 2 to the current input terminal 20 for conveying energy to the monopolar electrode 2. For example, the housing body 8 may include an electrically-conductive rod, wire or inner sleeve configured to electrically couple the electrode-engagement portion 25 with the current input terminal 20.

In embodiments, the attachment member 7A includes a ring member 9, or a partial ring member (e.g., 90 shown in FIG. 2B), which has an interior aperture defined therein and configured to be located on the middle segment of a surgeon's finger. Ring member 9 may include an interior aperture defined therein and configured to be located on the tip segment, or the base segment, of a user's finger. Ring member 9 may have any suitable inner diameter to accommodate fingers of different thicknesses. In embodiments, the ring member 9 may have an inner diameter "D1" in a range from about 0.10 inches to about 2.0 inches, an outer diameter "D2" in a range from about 0.15 inches to about 2.05 inches, and a thickness "T1" in a range from about 0.05 inches to about 0.30 inches. Ring member 9 may have an adjustable inner diameter.

Figure 2A:
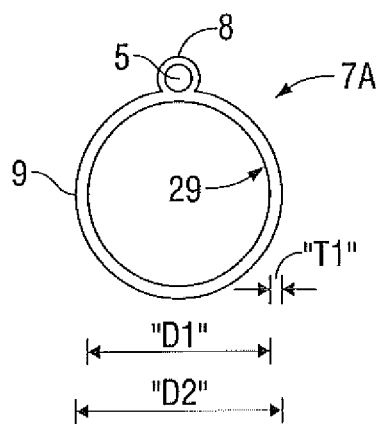
FIG. 2A is a schematic illustration of the attachment member of the fingertip, monopolar electrosurgical instrument of FIG. 1 according to an embodiment of the present disclosure.

As cooperatively shown in FIGS. 1 and 2A, the attachment member 7A may be integrally formed with the housing body 8. Attachment member 7A and the housing body 8 may be integrally formed by any suitable process, e.g., as part of a single molding process. Alternatively, the attachment member 7A and the housing body 8 may be formed separately from each other, and coupled together. Mechanical fasteners, adhesives, and welding processes, e.g., laser welding, or other suitable joining method may be used to attach (or clip, connect, couple, fasten, secure, etc.) the attachment member 7A to the housing body 8.

Ring member 9 may include an electrically non-conductive material to prevent (or at least substantially prevent) the conduction of electrical current through the ring member 9 to the surgeon's finger. Ring member 9 may be formed of any suitable electrically-insulative material, including, but not limited to, ceramics, mica, polyethylene, polyethylene terephthalate, polyimide, polytetrafluoroethylene (PTFE) (e.g., Teflon®, manufactured by E.I. du Pont de Nemours and Company of Wilmington, Del., United States), metal oxides or other suitable insulator, and may be formed in any suitable manner. As cooperatively shown in FIGS. 2A and 2C, the inner peripheral surface 29 of the ring member 9 may be provided with a material 22. Material 22 may be a soft-touch material to promote user comfort and/or reduce slip or spin of the ring member 9, e.g., to prevent unwanted movement of the housing body 8 and the electrode 2 associated therewith.

Figure 2B:
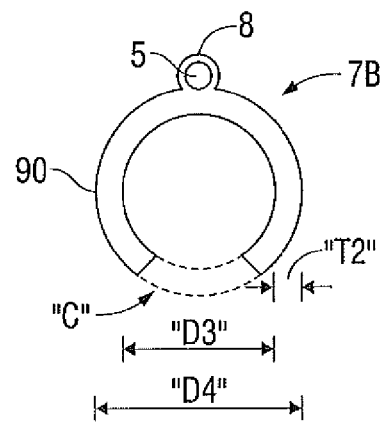
FIG. 2B is a schematic illustration of another embodiment of an attachment member of a fingertip, monopolar electrosurgical instrument in accordance with the present disclosure.
Figure 2C:
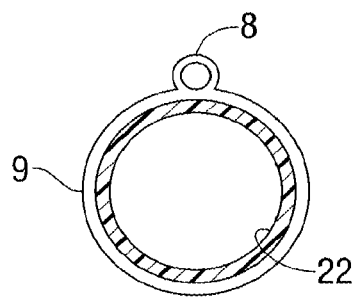
FIG. 2C is a schematic illustration of yet another embodiment of an attachment member of a fingertip, monopolar electrosurgical instrument in accordance with the present disclosure.
Figure 2D:
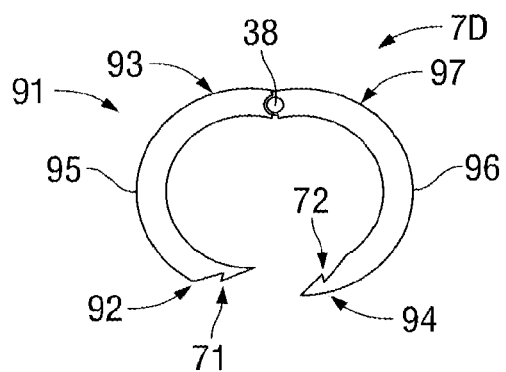
FIG. 2D is a schematic illustration of still another embodiment of an attachment member of a fingertip, monopolar electrosurgical instrument in accordance with the present disclosure.
Figure 2E:
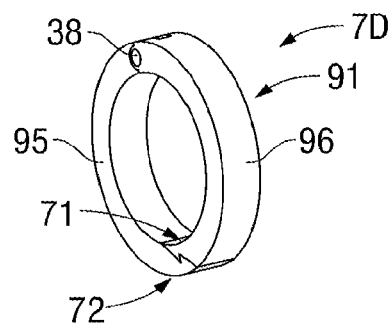
FIG. 2E is a perspective view of the attachment member of FIG. 2D shown with the ring member in a closed configuration according to an embodiment of the present disclosure.

An attachment member 71D configured with a hinged ring member 91 according to an embodiment of the present disclosure is shown in FIGS. 2D and 2E. Hinged ring member 91 is generally adapted to allow for ease of attachment of the presently disclosed fingertip, monopolar electrosurgical instrument to the user's finger. Ring member 91 is shown in an open configuration in FIG. 2D. In FIG. 2E, the ring member 91 is shown in a closed configuration.

Ring member 91 includes a first ring-member portion 95 including a first end 92 and a second end 93, and a second ring-member portion 96 including a first end 94 and a second end 97. A hinge member 38 is disposed between and moveably couples the second end 93 of the first ring-member portion 95 and the second end 97 of the second ring-member portion 96. First end 92 of the first ring-member portion 95 includes a first clasp element 71, and the first end 94 of the second ring-member portion 96 includes a second clasp element 72 adapted to be releaseably engageable with the first clasp element 71 when the ring member 91 is placed in the closed configuration.

Electrode 2 dimensions, e.g., thickness "W1" and length "L1", may be minimized, e.g., to facilitate a wide range of motion to allow for complex surgical articulation and/or to reduce trauma to the surgical site. In some embodiments, the energy applicator 12 includes a plurality of electrodes. The electrodes may have similar or different diameters, may extend to equal or different lengths, and may have a distal end with a tapered tip. In some embodiments, the one or more electrodes may be provided with a coolant chamber (not shown).

Fingertip, monopolar electrosurgical instrument 10 may include a temperature sensor (e.g., 31 shown in FIG. 3) configured to obtain temperature information associated with the electrode 2. Temperature sensor 31 may be disposed within the holder housing 8, and may be configured to contact the connector 4, or portion thereof (e.g., connector rod 6). The temperature sensor may be, for example, a thermocouple, a thermistor, or any other type of temperature sensing device capable of sending a signal indicative of a temperature of an electrode 2 portion to the electrosurgical power generating source 28 and/or to a processor unit (not shown). The processor unit may include any type of computing device, computational circuit, or any type of processor or processing circuit capable of executing a series of instructions that are stored in a memory associated with the processor unit.

Electrosurgical power generating source 28 may be any generator suitable for use with electrosurgical devices, and may be configured to provide various frequencies of electromagnetic energy. Examples of electrosurgical generators that may be suitable for use as a source of electrosurgical energy are commercially available under the trademarks FORCE EZ™, FORCE FX™, SURGISTAT™ II, and FORCE TRIAD™ offered by Covidien. Fingertip, monopolar electrosurgical instrument 10 may alternatively be configured as a wireless device.

In some embodiments, the electrosurgical power generating source 28 is configured to provide microwave energy at an operational frequency from about 300 MHz to about 2500 MHz. In other embodiments, the power generating source 28 is configured to provide microwave energy at an operational frequency from about 300 MHz to about 10 GHz. Electrosurgical power generating source 28 may be configured to provide various frequencies of electromagnetic energy.

In embodiments, the transmission line 11 may be formed from a suitable flexible, semi-rigid or rigid microwave conductive cable, and may connect directly to an electrosurgical power generating source 28. Transmission line 11 may include an inner conductor, a dielectric material coaxially surrounding the inner conductor, and an outer conductor coaxially surrounding the dielectric material. Transmission line 11 may additionally, or alternatively, provide a conduit configured to provide coolant fluid from a coolant source (not shown) to the energy applicator 12. In accordance herewith, temperatures at, or near the end portion 1 may be controlled by controlling the flow of coolant fluid through the electrode 2. In this manner, the temperature of the surface area of the end portion 1 in contact with tissue is controllable.

In operation when using an RF power supply, electrical current spreads from the electrode 2, or portion thereof, e.g., end portion 1, to pass through the surrounding tissue causing the tissue to heat up. In embodiments, the electrode 2 carries an electrically-insulative coating (not shown) over a portion of its length for selectively preventing the flow of electrical current from the shaft of electrode 2 into surrounding tissue. The electrically-insulative coating may shield the intervening tissue from RF current, so that tissue along the length of the shaft is not substantially heated except by the heating effect from the exposed end portion 1.

During a procedure, e.g., an ablation procedure, using the fingertip, monopolar electrosurgical instrument 10, the energy applicator 12 is inserted into or placed adjacent to tissue and energy, such as microwave or RF energy, is supplied thereto. A clinician may pre-determine the length of time that energy is to be applied. Application duration may depend on a variety of factors such as energy applicator design, number of electrodes used simultaneously, tumor size and location, and whether the tumor was a secondary or primary cancer. The duration of energy application using the energy applicator 12 may depend on the progress of the heat distribution within the tissue area that is to be destroyed and/or the surrounding tissue.

During a procedure, a return electrode (not shown) may be positioned in contact with the skin of the patient or a surface of the organ. When the surgeon activates the presently disclosed energy applicator 12, the return electrode may serve as a return current path for the current flowing from the power generating source 28 through the electrode 2.

Poor fit of an attachment member may lead to reduced user comfort and/or increased difficulty in using the presently disclosed fingertip, monopolar electrosurgical instruments. FIG. 2B shows an attachment member 7B of a fingertip, monopolar electrosurgical instrument in accordance with an embodiment of the present disclosure. Attachment member 7B includes a partial ring member 90 and includes a cut-out portion "C" (shown by the dashed lines in FIG. 2B) defining a void in the ring member 90, which may allow the ring member 90 to flex and expand in diameter, e.g., to accommodate fingers of different thicknesses, improve the ease of use and/or increase comfort of the wearer of the attachment member 7B. In embodiments, the ring member 90 may have an inner diameter "D3" in a range from about 0.10 inches to about 2.0 inches, an outer diameter "D4" in a range from about 0.15 inches to about 2.05 inches, and a thickness "T2" in a range from about 0.05 inches to about 0.30 inches. Ring member 90 may be made, entirely or in part, from a flexible, electrically non-conductive material, e.g., polyurethane or other elastic plastic material.

Figure 4:
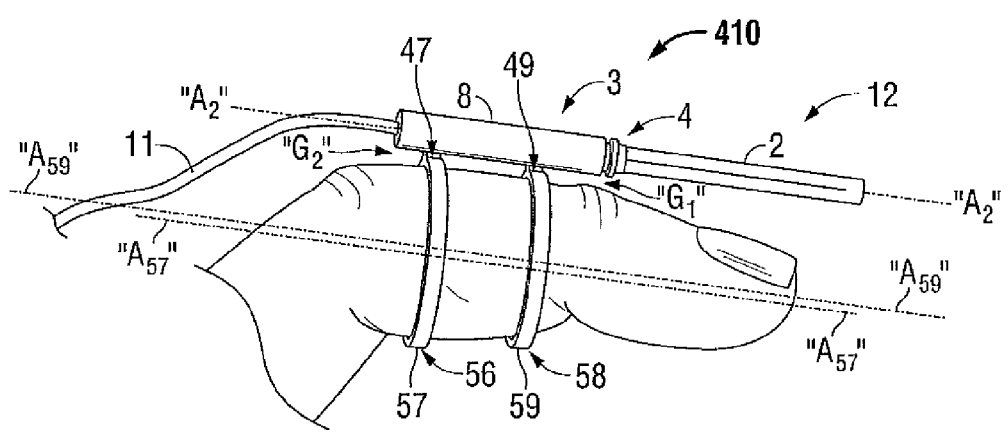
FIG. 4 is a perspective view of another embodiment of a fingertip, monopolar electrosurgical instrument shown coupled to a surgeon's finger in accordance with the present disclosure.

FIG. 4 shows a fingertip, monopolar electrosurgical instrument 410 coupled to a surgeon's finger according to an embodiment of the present disclosure that is similar to the fingertip, monopolar electrosurgical instrument 10 of FIGS. 1 and 3, except for the first and second attachment members 58 and 56, respectively.

Figure 5A:
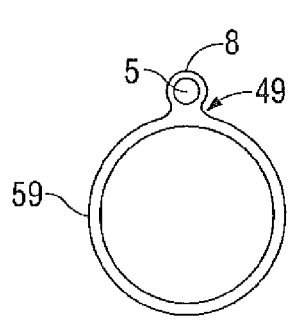
FIG. 5A is a schematic illustration of the first attachment member of the fingertip, monopolar electrosurgical instrument of FIG. 4 according to an embodiment of the present disclosure.
Figure 5B:
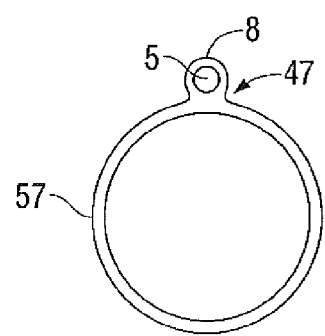
FIG. 5B is a schematic illustration of the second attachment member of the fingertip, monopolar electrosurgical instrument of FIG. 4 according to an embodiment of the present disclosure.

As cooperatively shown in FIGS. 4 and 5A, the first attachment member 58 is integrally formed with the housing body 8 and includes a first ring member 59 and a first neck portion 49. First neck portion 49 is configured to provide a first gap "$G_1$" between the housing body 8 and the surgeon's finger. As cooperatively shown in FIGS. 4 and 5B, the second attachment member 56 is integrally formed with the housing body 8 and includes a second ring member 57 and a second neck portion 47. Second neck portion 47 is configured to provide a second gap "$G_2$" between the housing body 8 and the surgeon's finger. First ring member 59 and the second ring member 57 may be formed of any suitable electrically-insulative material by any suitable process. The size and shape of the first and second ring members 59 and 57, respectively, and the first and second neck portions 49 and 47, respectively, may be varied from the configuration depicted in FIGS. 4 through 5B.

First neck portion 49 and the second neck portion 47 may have similar or different shapes, and may extend to equal or different lengths. In an embodiment the first and second neck portions 49 and 47, respectively, have substantially similar shapes and are configured with substantially equal lengths, to substantially align a longitudinal axis (e.g., "$A_2$-$A_2$" shown in FIG. 4) of the electrode 2 with the central longitudinal axis (e.g., "$A_{59}$-$A_{59}$" shown in FIG. 4) of the first ring member 59 and the central longitudinal axis (e.g., "$A_{57}$-$A_{57}$" shown in FIG. 4) of the second ring member 57. As shown in FIG. 4, in an embodiment where the first and second neck portions 49 and 47, respectively, have substantially equal lengths, the first gap "$G_1$" may be approximately equal to the second gap "$G_2$" such that the electrode 2 is aligned substantially parallel to the surgeon's finger, or segment thereof. The first gap "$G_1$" and/or the second gap "$G_2$" may be selectively adjusted by varying one or more dimensions, e.g., length, of the first neck portion 49 and/or the second neck portion 47, to permit angular adjustment of the electrode 2 with respect to the surgeon's finger, or particular segment(s) thereof.

Figure 6:
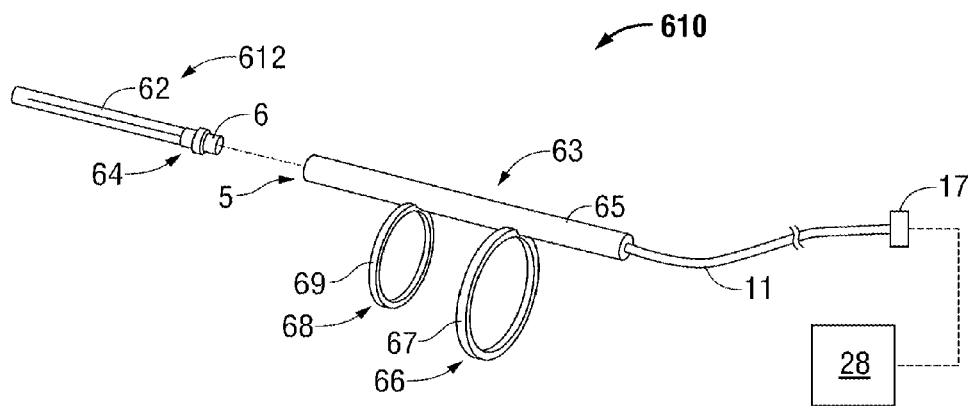
FIG. 6 is a perspective view of another embodiment of a fingertip, monopolar electrosurgical instrument, with parts separated, in accordance with the present disclosure.
Figure 7:
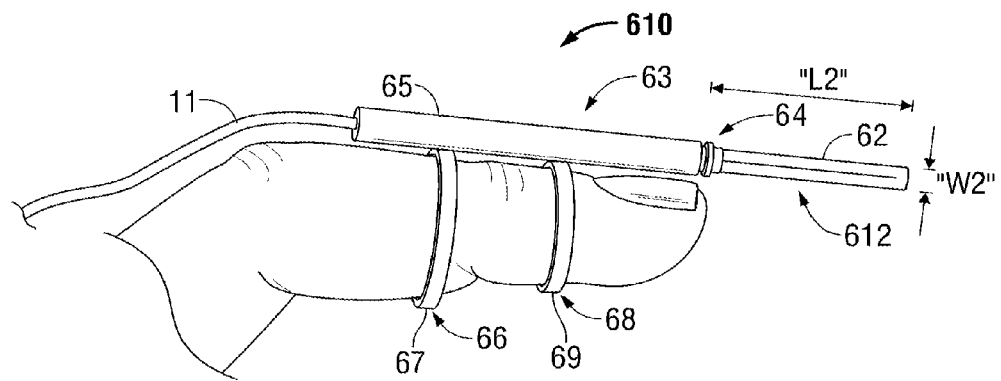
FIG. 7 is a perspective view of the fingertip, monopolar electrosurgical instrument of FIG. 6 shown coupled to a surgeon's finger according to an embodiment of the present disclosure.

FIG. 6 shows a fingertip, monopolar electrosurgical instrument 610 according to an embodiment of the present disclosure that includes an energy applicator 612 and a holder 63. FIG. 7 shows the presently disclosed fingertip, monopolar electrosurgical instrument 610 coupled to a surgeon's finger.

Energy applicator 612 includes a monopolar electrode 62 connected by the holder 63 via a transmission line 11 to a connector 17, which may further operably connect the energy applicator 612 to an electrosurgical power generating source 28, e.g., a microwave or RF electrosurgical generator. As cooperatively shown in FIGS. 6 and 7, the holder 63 is configured to support the energy applicator 612 such that the electrode 62 extends longitudinally from the distal end of the surgeon's fingertip. Monopolar electrode 62 may be removeably coupleable with the holder 63, and may be a standard blade electrode, ball electrode, needle electrode, spatula electrode, L-shape hook electrode, J-shape hook electrode, specialty electrode, or other suitable configuration. Monopolar electrode 62 may have a suitable length "L2" in a range from about 0.1 inches to about 3.0 inches. Electrode 62 may have a suitable width "W2" in a range from about 0.05 inches to about 0.5 inches. A connector 64 is located at the proximal end of the electrode 62. Electrode 62 and the connector 64 are similar to the electrode 2 and the connector 4, respectively, shown in FIG. 1 and further description thereof is omitted in the interests of brevity.

Holder 63 includes a housing body 65, a first attachment member 68 and a second attachment member 66. Housing body 65 is adapted to provide an electrical connection between the electrode 62 and the transmission line 11. First attachment member 68 includes a first ring member 69, which has an interior aperture defined therein. In embodiments, the aperture is configured to be located on the distal segment of a surgeon's finger. Second attachment member 66 includes a second ring member 67, which has an interior aperture configured to be located on the middle segment of a surgeon's finger. First and second ring members 69 and 67, respectively, may be formed of any suitable electrically-insulative material. The size, shape and relative spacing of the first ring member 69 and the second ring member 67 may be varied from the configuration depicted in FIG. 6.

As cooperatively shown in FIGS. 6 and 7, the holder 63 is configured to support the energy applicator 612 such that the electrode 62 extends from the distal end of the surgeon's fingertip. As shown in FIG. 7, a portion of the housing body 65, bridging between the first ring member 69 disposed on the distal side of the first knuckle and the second ring member 66 disposed on the proximal side of the first knuckle, spans across the first knuckle, which may provide a stabilizing influence on the surgeon's fingertip, which may enhance the surgeon's capability to point the monopolar electrode 62.

Figure 8:
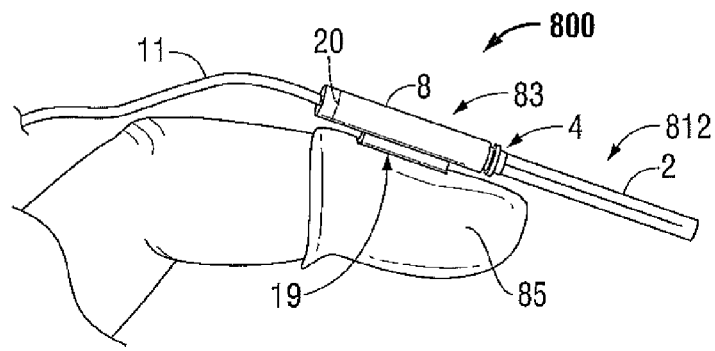
FIG. 8 is a perspective view of another embodiment of a fingertip, monopolar electrosurgical instrument in accordance with the present disclosure.

FIG. 8 shows a fingertip, monopolar electrosurgical instrument 800 according to an embodiment of the present disclosure that includes a fingertip sleeve 85, a holder 83 coupled to the fingertip sleeve 85, and an energy applicator 812 coupled to the holder 83. Energy applicator 812 is similar to the energy applicator 12 shown in FIG. 1 and further description thereof is omitted in the interests of brevity.

In embodiments, the fingertip sleeve 85 is configured to cover the tip segment and the first knuckle of the surgeon's finger, and may cover at least a portion of the middle segment. Fingertip sleeve 85 may be formed of a flexible, biocompatible material, e.g., one or more layers of a biocompatible, polymeric material.

Fingertip sleeve 85 generally includes a substantially tubular member having an open end and a closed end. The tubular member is adapted to receive a finger therein with the fingertip abutting the closed end. Fingertip sleeve 85 may be seamless. A releasable adhesive, or film layer having a high friction surface, may be distributed over at least a portion of the interior of the fingertip sleeve 85, e.g., to inhibit slippage of the sleeve from the surgeon's fingertip during a procedure.

Holder 83 is similar to the holder 3 shown in FIG. 1, except for the attachment member 19. In embodiments, the attachment member 19 may include one or more mechanical fasteners, e.g., a clip, for securely coupling the housing body 8 to the fingertip sleeve 25. Suitable adhesives, either alone or in combination with one or more mechanical fasteners, may be used as the attachment member 19. Attachment member 19 may be formed of suitable materials by any suitable process. The size and shape of the attachment member 19 may be varied from the configuration depicted in FIG. 8.

Figure 9:
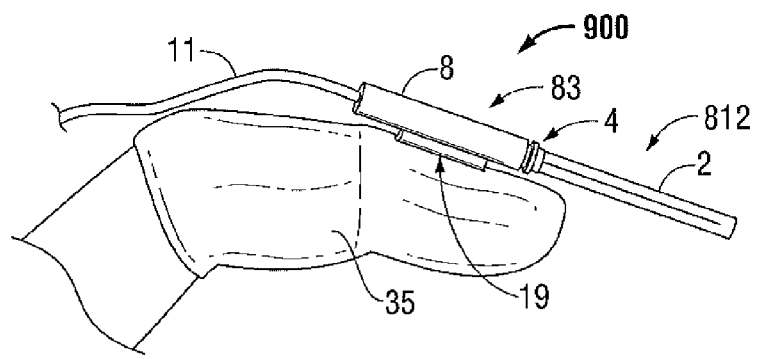
FIG. 9 is a perspective view of yet another embodiment of a fingertip, monopolar electrosurgical instrument in accordance with the present disclosure.

FIG. 9 shows a fingertip, monopolar electrosurgical instrument 900 according to an embodiment of the present disclosure that is similar to the fingertip, monopolar electrosurgical instrument 800 shown in FIG. 8, except for the configuration of the finger sleeve 35. Finger sleeve 35 is configured to cover the tip segment, first knuckle, second segment, and the second knuckle of the surgeon's finger, and may cover at least a portion of the third segment.

Figure 10:
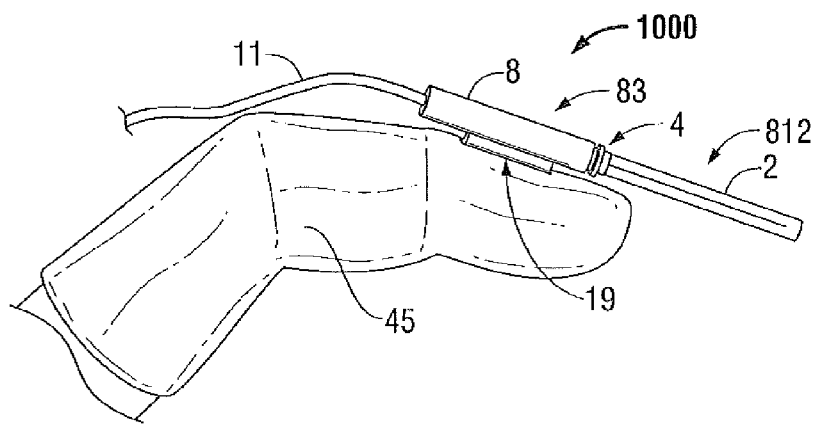
FIG. 10 is a perspective view of still another embodiment of a fingertip, monopolar electrosurgical instrument shown coupled to a surgeon's finger in accordance with the present disclosure.

FIG. 10 shows a fingertip, monopolar electrosurgical instrument 1000 according to an embodiment of the present disclosure that is similar to the fingertip, monopolar electrosurgical instrument 900 shown in FIG. 9, except for the configuration of the finger sleeve 45. Finger sleeve 45 is configured to cover the surgeon's entire finger, and may have a substantially tubular shape. Finger sleeve 45 may be configured to have a shape substantially conforming to a shape of a finger, and may include a liner, e.g., to enhance wearer comfort. Finger sleeve 45 provides an increased surface area in contact with the surgeon's finger, e.g., in comparison to the finger sleeve 35 shown in FIG. 9 and the fingertip sleeve 25 shown in FIG. 8, which may improve sleeve retention characteristics and/or provide enhanced insulative properties that help prevent the flow of electrical current from the electrode 2 into the surgeon's finger.

Fingertip sleeve 25, finger sleeve 35 and finger sleeve 45, and/or the holder 83 affixed thereto, may be discarded or recycled after a single use. Energy applicator 812 may be formed of stainless steel or other durable materials that are reusable and resterilizable.

Figure 11:
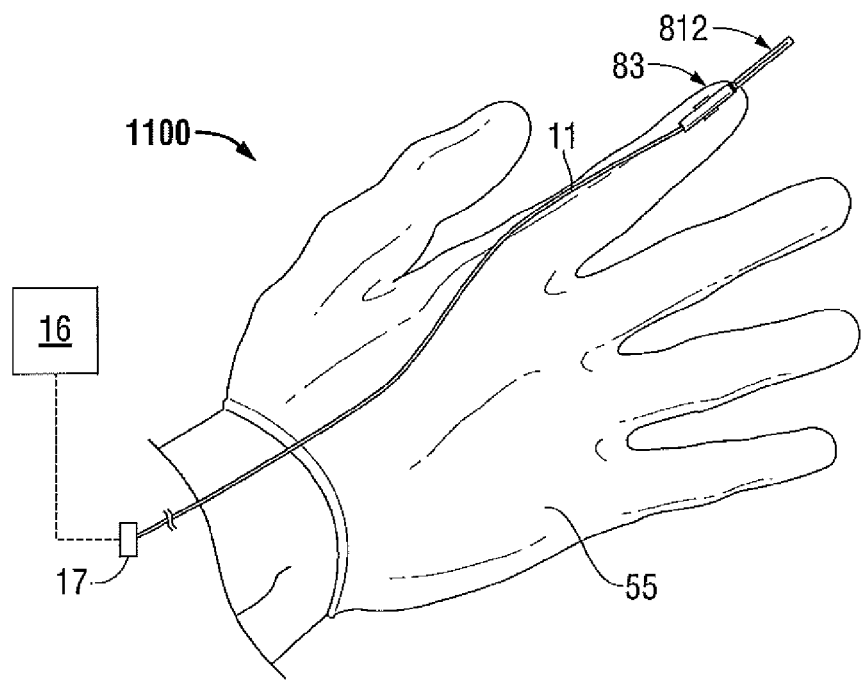
FIG. 11 is a perspective view of a fingertip, monopolar electrosurgical instrument including a surgical glove according to an embodiment of the present disclosure.

FIG. 11 shows a fingertip, monopolar electrosurgical instrument 1100 according to an embodiment of the present disclosure that is similar to the fingertip, monopolar electrosurgical instrument 1000 shown in FIG. 10, except for the surgical glove 55 that replaces the finger sleeve 45. Surgical glove 55 generally includes a hollow member defining an open proximal end for receiving a hand. Surgical glove 55 may be a surgical-quality latex glove, and may be available in a range of sizes, e.g., 300 mm and 375 mm sizes or other suitable sizes. Surgical glove 55 may have a multi-layered configuration having high tactility and dexterity characteristics including an outer shell fabricated from relatively flexible and durable material. Surgical glove 55 may include an elastic cuff, a liner, e.g., a terry seamless knitted liner, and/or a textured palm and fingertips. A film layer having a high friction surface may be distributed over at least a portion of the interior of the surgical glove 55, e.g., to minimize slippage and/or provide improved fluid barrier properties. Glove 55 may include an optional tightening device (not shown), such as fabric hook-and-loop (Velcro™) fasteners.

Fingertip, monopolar electrosurgical instrument 1100 includes the holder 83 and the energy applicator 812 coupled to the holder 83 of FIGS. 8 through 10. Holder 83 is coupled to the glove 25 by an attachment member (e.g., 19 shown in FIGS. 8 through 10). Suitable adhesives or other methods of attachment, either alone or in combination with one or more mechanical fasteners, may be used as the attachment member 19. Examples of adhesives that may be suitable include urethane, epoxy, and rubbery adhesives. Other methods of attachment that may be suitably employed include laser welding, heat seal bonding, sonic welding and stitching.

Energy applicator 812 is electrically connected by the holder 83 via a transmission line 11 to a connector 17, which may further operably connect the energy applicator 812 to an electrosurgical power generating source 16. Electrosurgical power generating source 16 may be any generator suitable for use with electrosurgical devices, and may be configured to provide various frequencies of electromagnetic energy, e.g., a microwave or RF electrosurgical generator.

Figure 12:
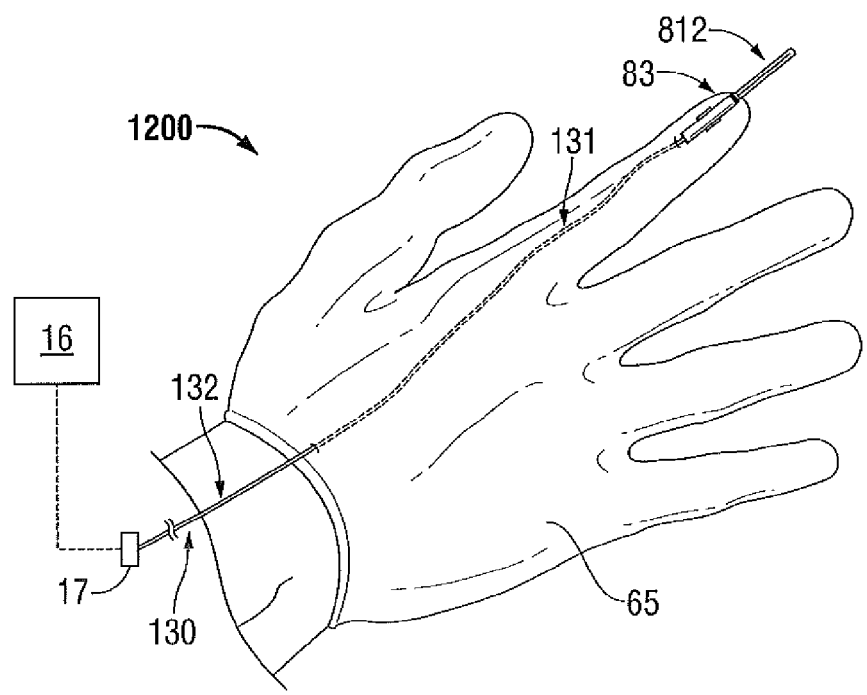
FIG. 12 is a perspective view of another embodiment of a fingertip, monopolar electrosurgical instrument including a surgical glove in accordance with the present disclosure.

FIG. 12 shows a fingertip, monopolar electrosurgical instrument 1200 coupled to a surgical glove according to an embodiment of the present disclosure that is similar to the fingertip, monopolar electrosurgical instrument 1100 of FIG. 11, except for the configuration of the transmission line 130. Transmission line 130 generally includes a first transmission-line portion 131 (shown by the dashed lines in FIG. 12) electrically coupled to the holder 83, and a second transmission-line portion 132 electrically coupled to the proximal end of the first transmission-line portion 131. First transmission-line portion 131 may be embedded within the glove, e.g., disposed between layers of the glove material, or disposed, entirely or in part, beneath the glove, which may improve usability characteristics of the fingertip, monopolar electrosurgical instrument 1200, e.g., during a procedure performed in confined spaces, where an exposed transmission line could potentially lead to tissue damage or otherwise impede surgical performance.

Figure 13:
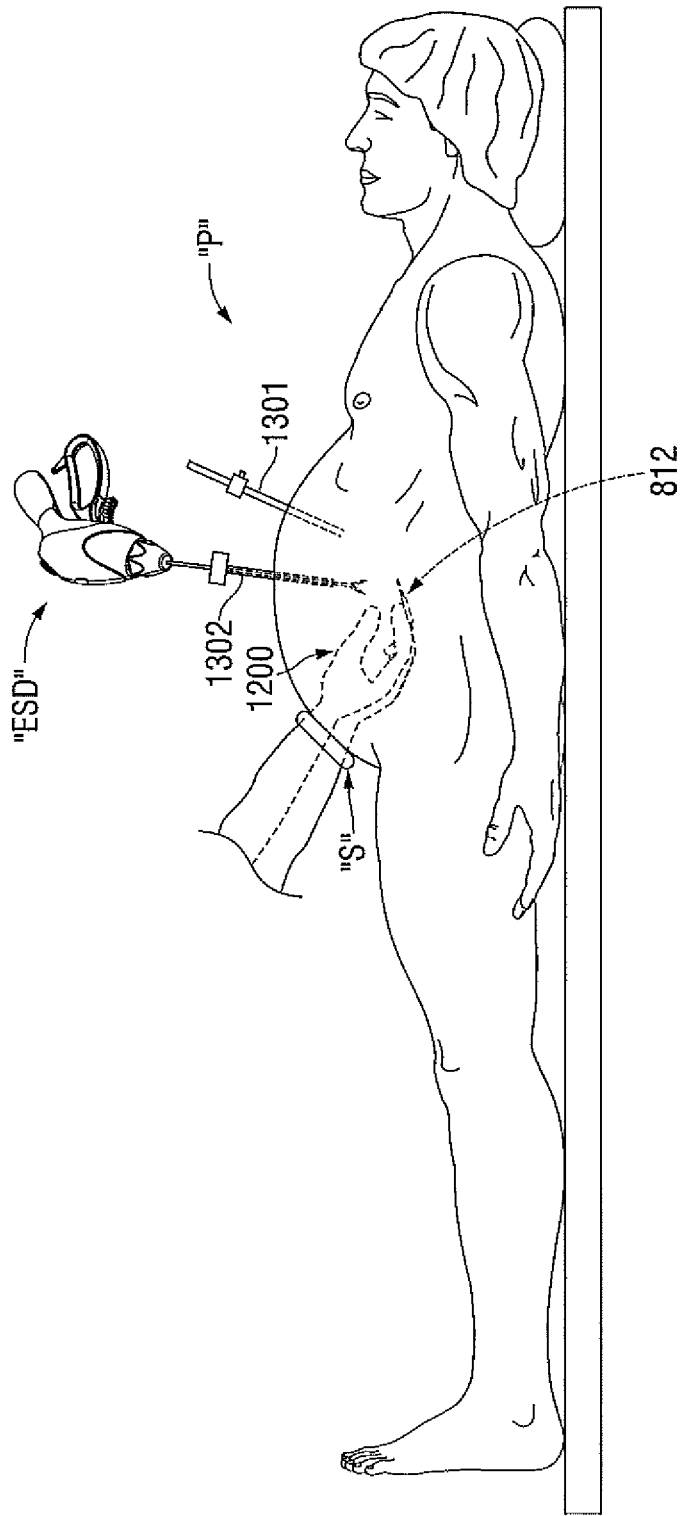
FIG. 13 is a perspective view of a patient in a supine position on an operating table with his abdomen insufflated, showing instrument access provided by two cannulae and hand access through an incision via a pressurized sleeve, and showing the fingertip, monopolar electrosurgical instrument of FIG. 12 according to an embodiment of the present disclosure.

FIG. 13 shows a patient "P" in a supine position on an operating table with his abdomen insufflated. Instrument access is provided by a first cannula 1301, which may include a connection for introducing an insufflation gas, and a second cannula 1302. A variety of instruments may be inserted through the first cannula 1301 and/or the second cannula 1302, including surgical instruments and electrosurgical devices (e.g., "ESD" shown in FIGS. 13 and 16). As shown in FIG. 13, hand access is provided by an access port defined by a pressurized sleeve "S" sealingly attached to tissue surrounding an incision. During a procedure the surgeon inserts a hand through the pressurized sleeve "S" into the insufflated region and uses the hand for sensory perception and to assist the laparoscopic instruments directly, while observing the entire procedure on a monitor (not shown).

As shown in FIG. 13, during a hand-assisted surgical procedure, the fingertip, monopolar electrosurgical instrument 1200 of FIG. 12 may be introduced via the pressurized sleeve "S" into the abdominal cavity. During certain procedures, the surgeon may activate the energy applicator 812 for directing energy into tissue. It is to be understood, however, that other fingertip, monopolar electrosurgical instrument embodiments (e.g., 10, 410, 610, 800, 900, 1000 and 1100 shown in FIGS. 3, 4, 7 8, 9, 10 and 11, respectively) may also be used.

Figure 14:
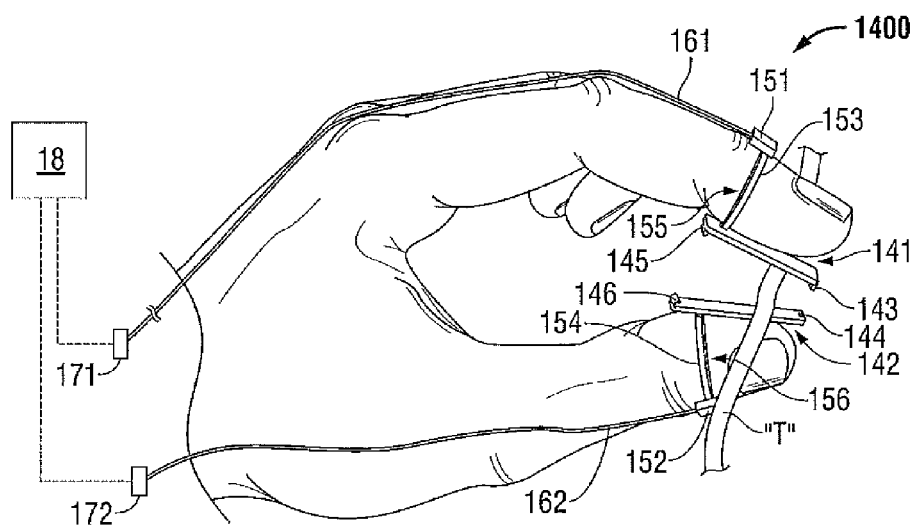
FIG. 14 is a perspective view of a fingertip, bipolar electrosurgical instrument according to an embodiment of the present disclosure.

FIG. 14 shows a fingertip, bipolar electrosurgical instrument 1400 according to an embodiment of the present disclosure that includes a first plate electrode 141 coupled via a first ring member to the surgeon's index finger (or other finger), and a second plate electrode 142 coupled via a second ring member to the surgeon's thumb. First plate electrode 141 and the second plate electrode 142 are generally configured to be used in an opposable relationship, e.g., to facilitate energy transfer and/or tissue grasping and releasing functions.

Using the fingertip, bipolar electrosurgical instrument 1400, sealing pressure applied to a vessel "T" may be varied over a wide range by a user-applied force, e.g., by squeezing the vessel "T" between the first plate electrode 141 and the second plate electrode 142. While the sealing pressure is applied, an electrical current can be run between the first plate electrode 141 and the second plate electrode 142 through the vessel "T" to coagulate, cauterize and/or seal the vessel "T".

First plate electrode 141 and the second plate electrode 142, according to various embodiments, are configured to enable the surgeon to achieve the proper or appropriate seal pressure. In embodiments, the first plate electrode 141 and the second plate electrode 142 are configured with one or more pair of opposed clip elements configured to limit the range of motion of the first plate electrode 141 and the second plate electrode 142 with respect to one another. First plate electrode 141 may include a first clip element 145 and a second clip element 143, and the second plate electrode 142 may include a third clip element 146 and a fourth clip element 144. First clip element 145 and the second clip element 143 may be disposed substantially adjacent to opposite ends of the first plate electrode 141, e.g., to maximize the available surface area therebetween on the first plate electrode 141 for contact with the patient's "P" tissue. Third clip element 146 and the fourth clip element 144 may be disposed substantially adjacent to opposite ends of the second plate electrode 142, e.g., to maximize the available surface area therebetween on the second plate electrode 142 for contact with the patient's "P" tissue.

In embodiments the first clip element 145 and the second clip element 143 may be configured to provide sensory and/or tactile feedback indicative of an appropriate sealing pressure has been achieved. First clip element 145 and the second clip element 143 may be configured to engage in a snap-fit manner with the third clip element 146 and the fourth clip element 144, respectively, which may provide tactile sensory feedback indicative of the appropriate sealing pressure has been achieved.

In embodiments, the first plate electrode 141, or portion thereof, and/or the second plate electrode 142, or portion thereof, may be formed of a black or dark-colored material, or anti-reflection coated, to minimize unwanted reflections. In embodiments, the first plate electrode 141 and/or the second plate electrode 142 may be formed of a substantially transparent material, e.g., to minimize unwanted reflections and/or enhance visualization of tissue disposed between the sealing plates. First plate electrode 141 and the second plate electrode 142 may take a variety of shapes, e.g., tapered or curved, depending upon multiple factors, such as, for example, the patient's anatomy, the type of surgical procedure, and preference of the surgeon and/or the patient.

In embodiments, the first plate electrode 141 is coupled to a first attachment member 151, and the second plate electrode 142 is coupled to a second attachment member 152. First plate electrode 141 is connected by the first attachment member 151 via a first transmission line 161 to a connector 171, which may further operably connect the first plate electrode 141 to an electrosurgical power generating source 18, Electrosurgical power generating source 18 may be any generator suitable for use with electrosurgical devices, and may be configured to provide various frequencies of electromagnetic energy. Second plate electrode 142 is connected by the second attachment member 152 via a second transmission line 162 to a connector 172, which may further operably connect the second plate electrode 142 to the electrosurgical power generating source 18.

First attachment member 151 includes a first ring member 153 including an interior aperture defined therein and configured on the tip segment of a finger. First ring member 153 may have any suitable inner diameter to accommodate fingers of different thicknesses. First ring member 153 may include an electrically non-conductive material disposed on an inner peripheral surface 155 of the first ring member 153. Second attachment member 152 includes a second ring member 154 including an interior aperture defined therein and configured on the tip segment of a finger. In embodiments, the second ring member 154 includes an electrically non-conductive material disposed on an inner peripheral surface 156 of the second ring member 154.

Figure 15:
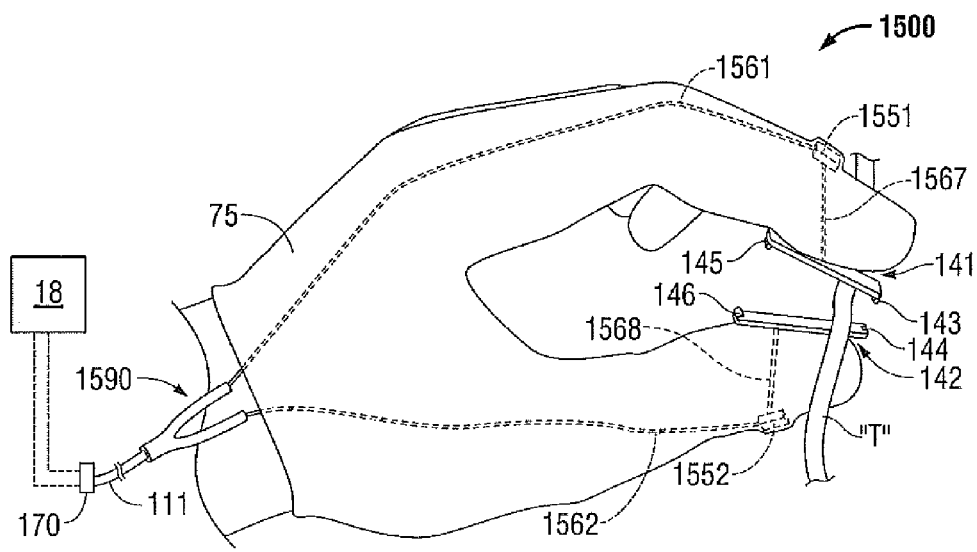
FIG. 15 is a perspective view of a fingertip, bipolar electrosurgical instrument including a surgical glove according to an embodiment of the present disclosure.

FIG. 15 shows a fingertip, bipolar electrosurgical instrument 1500 according to an embodiment of the present disclosure that includes a surgical glove 75, a first electrode plate 141, a second electrode plate 142, a first connector member 1551, and a second connector member 1552. Surgical glove 75 generally includes a plurality of finger sheaths configured to cover the configured to cover the surgeon's fingers. Fingertip, bipolar electrosurgical instrument 1500 may include one or more pair of opposed clip elements (e.g., first, second, third and fourth clip elements 145, 143, 146 and 144, respectively, shown in FIG. 14) configured to limit the range of motion of the first plate electrode 141 and the second plate electrode 142 with respect to one another. The clip elements may be configured to engage in a snap-fit manner to provide a tactile sensory feedback indicative of the appropriate sealing pressure has been achieved.

First electrode plate 141, which is capable of applying bipolar energy into tissue "T", is configured to be coupled to a first finger sheath of the surgical glove 75. Second electrode plate, which is capable of applying bipolar energy into tissue "T", is configured to be coupled to a second finger sheath of the surgical glove 75. First connector member 1551, which is associated with the first finger sheath, is electrically coupled via a transmission line 1567 to the first electrode plate 141. In embodiments, the first connector member 1551 may include the first ring member 153 shown in FIG. 14, which may be embedded in the surgical glove 75. Second connector member 1552, which is associated with the second finger sheath, is electrically coupled via a transmission line 1568 to the second electrode plate 142. In embodiments, the second connector member 1552 may include the second ring member 154 shown in FIG. 14, which may be embedded in the surgical glove 75.

In embodiments, the surgical glove 75 includes a material having a high level of puncture and cut resistance, e.g., a weave or knit of a material such as Kevlar, nylon or fiberglass. Surgical glove 75 may additionally, or alternatively, be formed of a material including a nonporous membrane that is substantially impermeable to fluids, e.g., blood. Surgical glove 75 may be formed of a material having oxygen permeability of at least 100 barrers. Surgical glove 75 may be formed of an ultra-thick material to provide a more effective insulator, e.g., to give an appropriate level of protection to the user.

In embodiments, the surgical glove 75 may be formed of a material that hydrates slowly. A glove that has become hydrated may measure a lower electrical resistance than a non-hydrated glove. A surgical glove that hydrates slowly may offer added protection against electrical shock and undesired burns.

As shown in FIG. 15, at least a portion of the first and second electrode plates 141 and 142, respectively, is disposed in contact with an outer surface of the surgical glove. First plate electrode 141 is connected by the first connector member 1551 via a transmission line 1561 to a connector 170, which further operably connects the first plate electrode 141 to a first pole of an electrosurgical power generating source 18, e.g., a microwave or RF electrosurgical generator. In embodiments, the first connector member 1551 and the transmission line 1561 are embedded in the surgical glove 75 (as indicated by dashed lines in FIG. 15). Second plate electrode 142 is connected by a second connector member 1552 via a transmission line 1562 to the connector 170, which further operably connects the second plate electrode 142 to a second pole of the electrosurgical power generating source 18. In embodiments, the second connector member 1552 and the second transmission line 1562 are embedded in the surgical glove 75 (as indicated by dashed lines in FIG. 15).

Proximal ends of the transmission lines 1561 and 1562 may be coupled to a junction member 1590. Junction member 1590 may be configured to be detachably coupleable to a transmission line 111, which may further operably connect the transmission lines 1561 and 1562 to a connector 170. Junction member 1590, or portion thereof, may be embedded or otherwise attached to the surgical glove 75.

Figure 16:
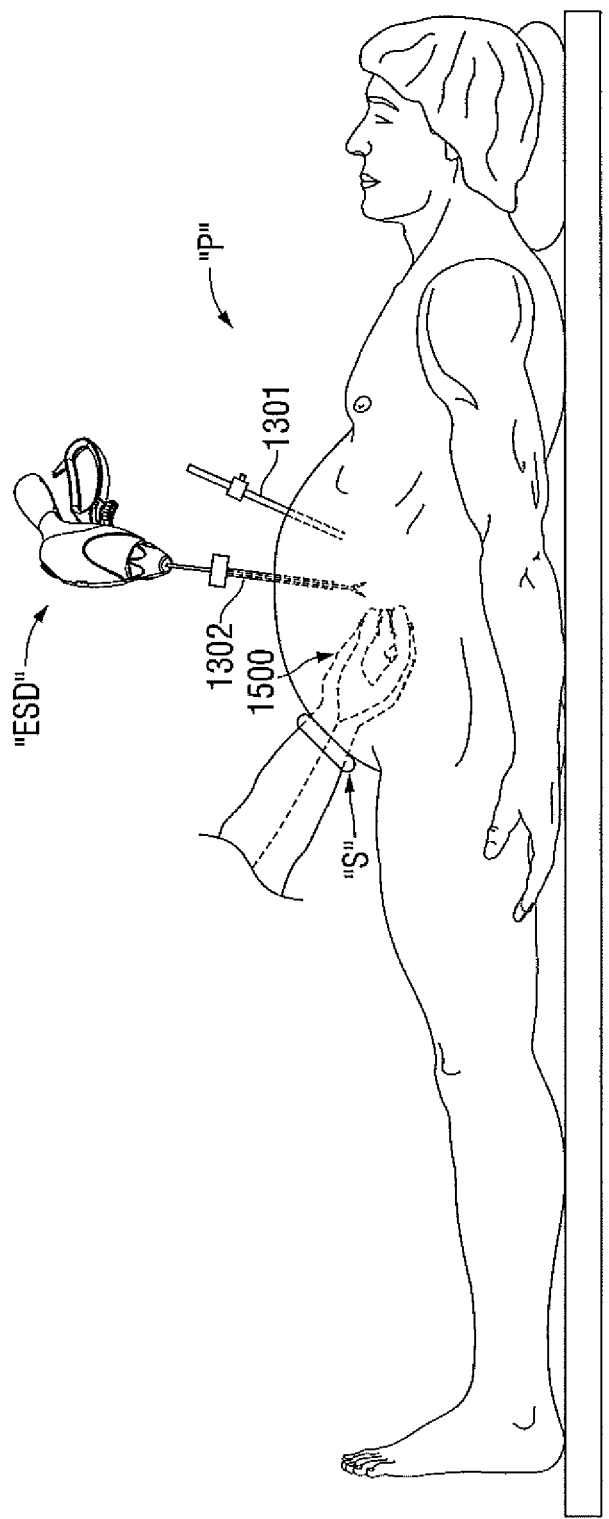
FIG. 16 is a perspective view of a patient in a supine position on an operating table with his abdomen insufflated, showing instrument access provided by two cannulae and hand access through an incision via a pressurized sleeve, and showing the fingertip, bipolar electrosurgical instrument of FIG. 15 according to an embodiment of the present disclosure.

FIG. 16 shows a patient "P" in a supine position on an operating table with his/her abdomen insufflated. Instrument access is provided by a first cannula 1301, which may include a connection for introducing an insufflation gas, and a second cannula 1302. A variety of instruments may be inserted through the first cannula 1301 and/or the second cannula 1302, e.g., electrosurgical device "ESD". As shown in FIG. 16, hand access is provided by a pressurized sleeve "S". During a procedure the surgeon inserts a hand through the pressurized sleeve "S" into the insufflated region and uses the hand for sensory perception and to assist the laparoscopic instruments directly, while observing the entire procedure on a monitor (not shown).

As shown in FIG. 16, during a hand-assisted surgical procedure, the fingertip, bipolar electrosurgical instrument 1500 of FIG. 15 may be introduced via the pressurized sleeve "S" into the abdominal cavity for directing energy into tissue, e.g., to effect vessel sealing, at times during the procedure. It is to be understood, however, that other fingertip, bipolar electrosurgical instrument embodiments (e.g., 1400 shown in FIG. 14) may also be used.

Figure 17:
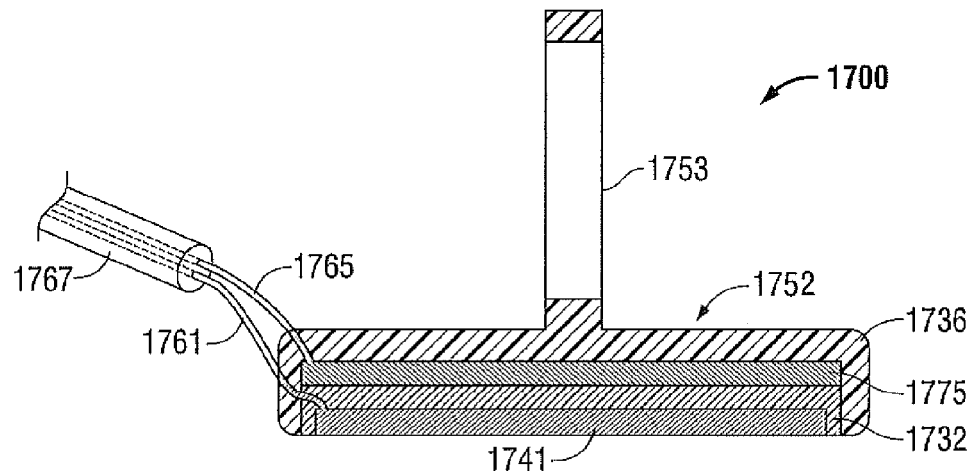
FIG. 17 is a perspective view of another embodiment of a fingertip, bipolar electrosurgical instrument in accordance with the present disclosure.

FIG. 17 shows a sealing member 1700 according to an embodiment of the present disclosure that includes a plate electrode 1741. Sealing member 1700 generally includes a ring member 1753 and a seal plate assembly 1752 coupled thereto. Ring member 1753 is similar to the ring member 155 of shown in FIG. 14 and further description thereof is omitted in the interests of brevity.

Seal plate assembly 1752 includes a plate electrode 1741 and a strain gage or load cell 1775 (herein referred to as a strain gage). Plate electrode 1741 is configured to be operably coupled to an electrosurgical power generating source 18. In some embodiments, the plate electrode 1741 is electrically coupled to the electrosurgical power generating source 18 via a wire 1761. Wire 1761 is electrically coupled to the plate electrode 1741 by any suitable manner of electrical connection, e.g., soldering, welding, or laser welding.

Strain gage 1775 is disposed generally parallel to the plate electrode 1741 with a first electrically-insulative material 1732 disposed therebetween. Strain gage 1775 may be configured to be operably coupled to a processor unit (not shown) via a wire 1765. Wire 1765 (and/or wire 1761) may be integrated into a multi-wire cable assembly 1767. Processor unit may include any type of computing device, computational circuit, or any type of processor or processing circuit capable of executing a series of instructions that are stored in a memory (not shown) associated with the processor unit, which may be in communication with a display device (not shown), such as without limitation a flat panel graphic LCD (liquid crystal display), and/or a visual signal indicator 1800, which is shown in more detail in FIG. 18. Strain gage 1775 may be a ¼, ½, full bridge strain gage or any combination to obtain the desired tolerance. In some embodiments, the force range for the strain gage 1775 may be from about 5 psi (pounds per square inch) to about 300 psi. A second electrically-insulative material 1736 may be disposed about the strain gage 1775, and may be configured to enclose the first electrically-insulative material 1732. Strain gage 1775 may be used in one or more sealing members 1700 of a fingertip, bipolar electrosurgical instrument in accordance with the present disclosure. For example, the use of two plate electrodes 1741 each configured with the strain gage 1775 may allow for increased accuracy of the force measurement.

Fingertip, bipolar electrosurgical instruments in accordance with the present disclosure may include two sealing members 1700. In some embodiments, the fingertip, bipolar electrosurgical instrument may be configured to signal the user (e.g., via visual signal indicator 1800 shown in FIG. 18) to activate the plate electrodes 1741, or automatically activate the plate electrodes 1741, when the appropriate sealing pressure is reached between the plate electrodes 1741 of the two sealing members 1700. Fingertip, bipolar electrosurgical instruments in accordance with the present disclosure may include two sealing members 1700 embedded in a glove, e.g., similar to the fingertip, bipolar electrosurgical instrument 1500 shown in FIG. 15.

Figure 18:
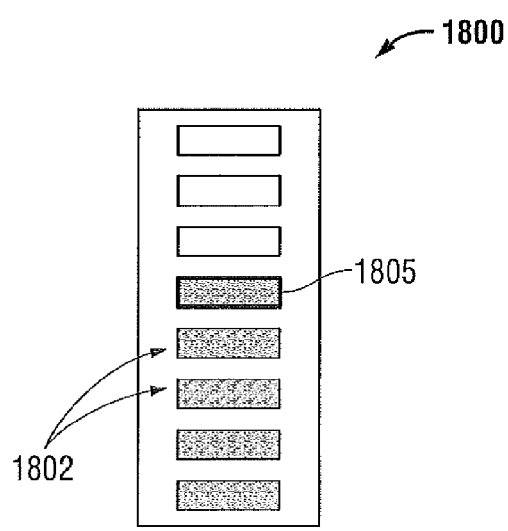
FIG. 18 is a schematic illustration of a visual signal indicator according to an embodiment of the present disclosure.

FIG. 18 is a schematic illustration of a visual signal indicator 1800 capable of emitting light signals indicatory of a sealing pressure range according to an embodiment of the present disclosure. In some embodiments, the visual signal indicator 1800 includes one or more light-emitting devices 1802, e.g., light-emitting diodes (LEDS), capable of emitting light signals indicatory of a sealing pressure range. Visual signal indicator 1800 may be configured with one light-emitting device 1805 (outlined in bold in FIG. 18) indicatory of an "optimal sealing pressure" condition when lighted, or flashing. In some embodiments, the visual signal indicator 1800 may be a bar graph displayed on a display device (not shown).

Various embodiments of the presently disclosed fingertip, monopolar and bipolar electrosurgical instruments may be suitable for use in a variety of procedures and operations. The above-described electrosurgical instrument embodiments may be suitable for utilization with hand-assisted, endoscopic and laparoscopic surgical procedures. The above-described electrosurgical instrument embodiments may be suitable for utilization in open surgical applications.

The above-described electrosurgical instruments may potentially reduce procedure time. Having the presently disclosed electrosurgical instruments at the surgical site may reduce the number of times the surgeon's hand is extracted and re-inserted through an access port for performing surgical procedures within an insufflated body cavity and/or minimize the need for instrument removal and re-insertion to change instruments in the laparoscopic ports. The above-described electrosurgical instruments may enhance the suitability of laparoscopy for complex abdominal surgery.

The above-described fingertip, monopolar electrosurgical instruments may offer the ability to perform more complex operations more safely by allowing tactile sensory feedback and depth perception. Various embodiments of the presently disclosed fingertip, monopolar electrosurgical instruments are capable of directing energy into tissue, and may be suitable for a variety of procedures, e.g., ablation procedures.

Various embodiments of the presently disclosed fingertip, bipolar electrosurgical instruments are capable of directing energy into tissue, and may be useful for a variety of operations, e.g., vessel sealing, tissue grasping and tissue cutting, coagulating, cauterizing and ablating, in open and laparoscopic surgical applications. Fingertip, bipolar electrosurgical instruments capable of vessel sealing during a HALS procedure may improve the reaction time to stop bleeding.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A fingertip-mountable electrosurgical instrument, comprising:
a monopolar electrode capable of directing energy into tissue;
a connector electrically coupled to the monopolar electrode; and
a holder including an engagement portion configured to be operably and electrically coupled to the monopolar electrode via the connector, and an input terminal electrically coupled to the engagement portion and configured to supply current from an energy source, the holder further including a housing body and at least one attachment member coupled to the housing body,
wherein the at least one attachment member is configured to be removeably attachable to a user's finger,
wherein the housing body has a distal end and a proximal end,
wherein the engagement portion is disposed at the distal end of the housing body and the input terminal is disposed at the proximal end of the housing body, and
wherein the connector is configured to be releasably engageable with the engagement portion.

2. The fingertip-mountable electrosurgical instrument of claim 1,
wherein the input terminal is coupled to the energy source via a transmission line.

3. The fingertip-mountable electrosurgical instrument of claim 1, wherein the at least one attachment member includes a ring member including an aperture defined therein, the aperture configured to receive a finger of a user.

4. The fingertip-mountable electrosurgical instrument of claim 3, wherein the ring member includes an electrically non-conductive material.

5. The fingertip-mountable electrosurgical instrument of claim 4, wherein the electrically non-conductive material is disposed on an inner peripheral surface of the ring member.

6. The fingertip-mountable electrosurgical instrument of claim 1, wherein the connector includes a rod-shaped portion configured to be releasably engageable with the engagement portion.

7. The fingertip-mountable electrosurgical instrument of claim 1, further comprising:
a temperature sensor configured to obtain temperature information associated with the monopolar electrode.

8. The fingertip-mountable electrosurgical instrument of claim 1, wherein the at least one attachment member includes a neck portion configured to provide a gap between the housing body and the user's finger.

9. The fingertip-mountable electrosurgical instrument of claim 1, wherein the at least one attachment member includes a first attachment member and a second attachment member, the first attachment member includes a first ring member, and the second attachment member includes a second ring member.

10. The fingertip-mountable electrosurgical instrument of claim 9, wherein the first ring member is configured to be coupled to a tip segment of the user's finger, and the second ring member is configured to be coupled to a middle segment of the user's finger.

11. The fingertip-mountable electrosurgical instrument of claim 9, wherein the first attachment member further includes a first neck portion coupled to the first ring member configured to provide a first gap between the housing body and the user's finger, and the second attachment member further includes a second neck portion coupled to the second ring member configured to provide a second gap between the housing body and the user's finger.

12. The fingertip-mountable electrosurgical instrument of claim 1, wherein the attachment member includes a sleeve element configured to cover at least a portion of the user's finger.

13. The fingertip-mountable electrosurgical instrument of claim 12, wherein the sleeve element is configured to cover at least a tip segment of the user's finger.

14. The fingertip-mountable electrosurgical instrument of claim 12, wherein the sleeve element is configured to cover a tip segment and at least a portion of a middle segment of the user's finger.

15. The fingertip-mountable electrosurgical instrument of claim 12, wherein the sleeve element is configured to cover a tip segment, a middle segment and at least a portion of a base segment of the user's finger.

16. The fingertip-mountable electrosurgical instrument of claim 1, wherein the connector includes a first end portion and a second end portion opposite the first end portion,
   wherein the monopolar electrode is coupled to the connector via the first end portion, and
   wherein the connector is configured to be releaseably engageable with the engagement portion via the second end portion of the connector.

17. An electrosurgical instrument, comprising:
   a surgical glove;
   a monopolar electrode capable of directing energy into tissue;
   a connector electrically coupled to the monopolar electrode; and
   a holder including an engagement portion configured to be operably and electrically coupled to the monopolar electrode via the connector, and an input terminal electrically coupled to the engagement portion and configured to supply current from an energy source, the holder further including a housing body and at least one attachment member coupled to the housing body,
   wherein the attachment member is configured to couple the holder to the surgical glove,
   wherein the housing body has a distal end and a proximal end,
   wherein the engagement portion is disposed at the distal end of the housing body and the input terminal is disposed at the proximal end of the housing body, and
   wherein the connector is configured to be releaseably engageable with the engagement portion.

18. An electrosurgical system, comprising:
   an energy source;
   a fingertip-mountable electrosurgical instrument operably coupled to the energy source, including:
   a monopolar electrode capable of directing energy into tissue;
   a connector electrically coupled to the monopolar electrode; and
   a holder including an engagement portion configured to be operably and electrically coupleable with the monopolar electrode via the connector and an input terminal electrically coupled to the engagement portion and configured to supply current from an energy source, the holder further configured to support the monopolar electrode such that the monopolar electrode extends longitudinally from a distal end of a user's fingertip,
   wherein the holder includes a housing body and at least one attachment configured to receive a user's finger,
   wherein the housing body has a distal end and a proximal end,
   wherein the engagement portion is disposed at the distal end of the housing body and the input terminal is disposed at the proximal end of the housing body, and
   wherein the connector is configured to be releaseably engageable with the engagement portion.

19. The electrosurgical system of claim 18, further comprising
   an external monopolar RF electrode configured to provide a return path for applied RF current.

* * * * *